United States Patent [19]

Cohen et al.

[11] 4,083,985

[45] Apr. 11, 1978

[54] 6-OXA-1-AZA TRICYCLO DODECAN-5-ONES AS PSYCHOMOTOR STIMULATORS

[75] Inventors: Sasson Cohen, Tel-Aviv; Abraham Fisher, Holon, both of Israel

[73] Assignee: The Purdue Frederick Company, New York, N.Y.

[21] Appl. No.: 655,650

[22] Filed: Feb. 6, 1976

[30] Foreign Application Priority Data

Nov. 11, 1975  Israel ......................................... 48453

[51] Int. Cl.² .................. C07D 491/04; A61K 31/535
[52] U.S. Cl. ............................... 424/267; 260/293.53; 260/289 H
[58] Field of Search ..................... 260/293.53; 424/267

[56] References Cited

U.S. PATENT DOCUMENTS 3,857,837  12/1974  Gutzwiller et al. ............. 260/240 R

*Primary Examiner*—John M. Ford
*Attorney, Agent, or Firm*—Harold D. Steinberg; Alfred Halpern

[57] ABSTRACT

Compounds of the general formula

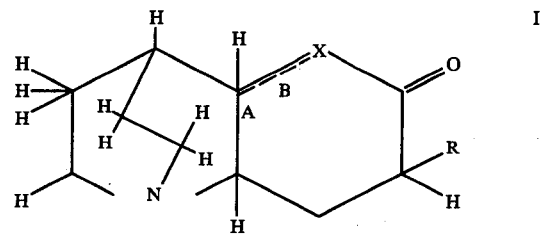

wherein X is selected from the group consisting of oxygen $CH_2$ and CH radicals, and when X designates oxygen, R designates alkyl, isoalkyl, aralkyl, and substituted aryl groups and when X designates

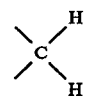

then R designates alkyl, phenyl or substituted phenyl group, and A—B is a single bond and when X designates >CH, and A—B is a double bond, R designates alkyl, phenyl or substituted phenyl groups and physiologically acceptable salts of these, and pharmaceutical compositions containing same as active ingredient.

15 Claims, No Drawings

6-OXA-1-AZA TRICYCLO DODECAN-5-ONES AS PSYCHOMOTOR STIMULATORS

SUMMARY OF THE INVENTION

The present invention relates to novel compound of the general formula:

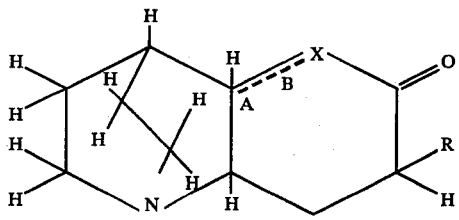

wherein X may be oxygen, $CH_2$ and CH groups; R may be alkyl, isoalkyl, phenyl and substituted phenyl groups such as methoxyphenyl, chlorophenyl, methylphenyl and benzyl group, and when X is the $CH_2$ group, then A–B is a single bond; and when X is the CH group, then A–B is a double bond.

Compounds defined above, wherein X designates =O comprise the fused quinuclidine-valerolactone system, 6-oxa-1-azatricyclo (6.2.2.0$^{2,7}$)-dodecan-5-one, alkylated congeners of these and salts of such compounds. This comprises various stereo-isomers and optically active isomers of such compounds and salts. These are of the general formula:

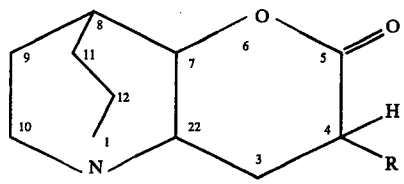

wherein R is as defined above.

Compounds defined above, wherein X designates

or CH, and wherein R designates phenyl or substituted phenyl or alkyl are of the formula

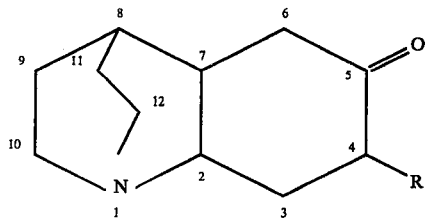

wherein there is an optional 6-7-double-bond, and R is alkyl, phenyl or substituted phenyl, the preferred compound being the one wherein R is ethyl or phenyl.

The present invention relates also to pharmaceutical preparations comprising a compound or salt as defined above as active ingredient.

The term "alkyl" relates to groups such as methyl, ethyl, propyl, butyl; the term isoalkyl defines groups such as isopropyl, isobutyl; cycloalkyl defines groups such as cyclopentyl, cyclohexyl. Representative aryl or heteroaryl groups are phenyl or thienyl; substituted aryl designates such groups as chlorophenyl, methoxy phenyl, trifluoromethylphenyl and amino-phenyl, or N,N-substituted aminophenyl, where N,N— is dilower alkyl.

The invention comprises salts of the above, which are suitable for pharmaceutical or veterinary application, and also to salts useful in the purification and crystallization of the novel compounds. Amongst such salts there may be mentioned the hydrochlorides, sulfates, methanesulfonates and salts with organic acids.

Amongst N-alkyl congeners there may be mentioned N-methyl, N-ethyl, N-benzyl compounds, especially in the form of the iodides, bromides or chlorides.

Starting compounds useful in the preparation of compounds (II) of the present invention of the 4-alkyl-6-oxa-1-azatricyclo-(6.2.2.0$^{2,7}$) dodecan-5-one type are monosubstituted esters of malonic acid, such as diethyl methylmalonate, diethyl-ethylmalonate, diethyl propylmalonate, diethyl isopropylmalonate, diethyl n-butylmalonate, diethylbenzylmalonate and the like. Starting materials for the preparation of 4-aryl-6-oxa-1-azatricyclo (4.2.2.0$^{2,7}$) dodecan-5-one type compounds are ortho- meta- and para-substituted esters of phenylacetic acid, such as ethyl p-methylphenylacetate, ethyl m-methoxyphenylacetate or substituted phenylacetonitriles, such as p-chlorophenylacetonitrile.

Compounds of the formula (III) are prepared in two steps by reacting 2-methylene-quinuclidin-3-one and methyl benzylketone followed by selective catalytic reductions.

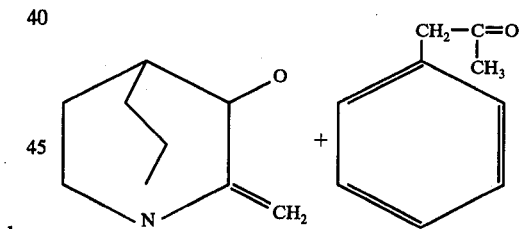

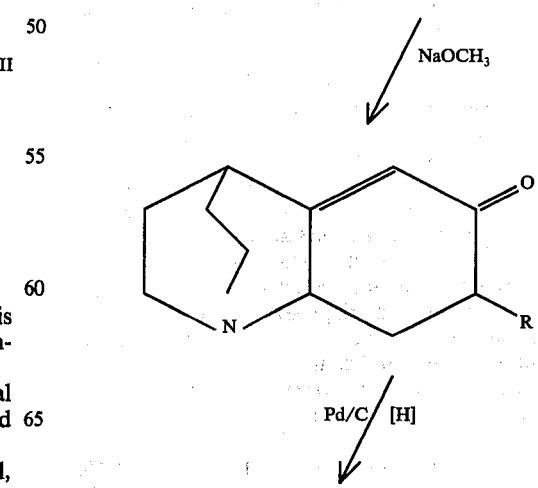

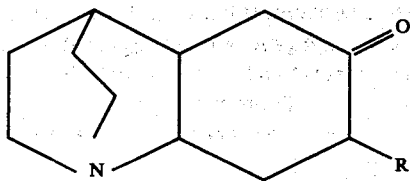

or in three steps, by condensation of 2-methylene-3-quinuclidinone with a substituted ethylacetoacetate, followed by decarboxylation and subsequent reduction, as set out in the following reaction scheme:

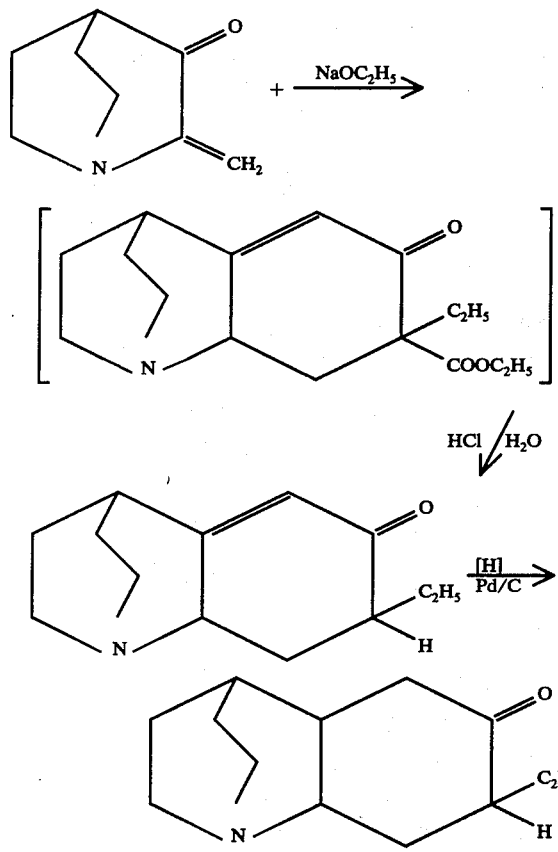

The compounds according to the present invention are valuable as active ingredients in pharmaceutical compositions of matter. They are valuable as drugs, in the treatment and in the alleviation of the manifestations of Parkinson's diseases; they are effective general psychomotor stimulants, and as such they are of special value in geriatrics. The compounds of the present invention can be used as antimotion sickness drugs, they are of value in opthalmology as mydriatics. They can be used in smoking abstinence treatments including exaggerated effects of tobacco. The compounds of the present invention are effective "wake-up" agents, and as such they can be used to correct the depressant effect of barbiturates. They can be used to counter the effect of drowsiness of antihistaminics and similar drugs.

They are also useful in the treatment of hyperkinesis in children, of narcolepsy, of mental depression of organic origin and of obesity.

The dosage is generally of about 10 mg to about 100 mg for an adult per day. The drugs according to the present invention can be given by way of injection in a suitable diluent or carrier, the drugs can be given per os, in the form of suppositories and by any other conventional manner of application, such as infusion, etc.

The compounds of the present invention are of special value when used in combination with antihistminics to be used during day-time, as the resulting composition is devoid of the effect of drowsiness of the person thus treated.

When applied for opthalmological use, the drugs of the present invention are advantageously used in a conventional carrier of buffer. The concentrations can be varied according to the desired effect, and they will be generally about 2 to 10% by weight of the active ingredient.

The present invention relates also to pharmaceutical and veterinary compositions of matter comprising any of the novel compounds of the invention, or combinations of any of these, as active ingredient.

The invention also relates to stereoisomers and optical isomers of the compounds defined above, such isomers being due to the asymetry at the carbon atoms in the 2-, 4- and 7-positions as defined above in the respective compounds (II), or in positions 2, 4, and 7 in compounds III where $C_6$-$C_7$ is a single bond.

DESCRIPTION OF THE PREFERRED EMBODIMENT

The following examples are intended to illustrate the present invention and these are to be construed in a non-limitative manner.

EXAMPLE 1

Ethanolic sodium ethoxide, previously prepared from 2.9 g of metallic sodium and 100 ml of ethanol, was added to diethyl methyl-malonate, 50 g, and the mixture was refluxed for 30 min. then cooled to 5°. A solution of 2-methylenequinuclidin-3-one, 39.4 g, in ethanol, 50 ml, was then added dropwise and with stirring. After 16 hrs. at room temperature, the resulting solution was neutralized with acetic acid then subjected to evaporation at reduced pressure. Water, 100 ml was added and the mixture was extracted with chloroform. Evaporation of this solvent gave diethyl (3-oxo quinuclidin-2-yl)methyl-methylmalonate, 72 g (81%), m.p., 58.4° (from petroleum ether).

A solution of the foregoing compound, 72 g, in ethanol, 50 ml, was treated at 5° and with stirring with a solution of sodium borohydride, 3.55 g, in ethanol, 600 ml. The borohydride solution was added in small increments over a period of 6 hours. After 20 hours, the mixture was neutralized with concentrated hydrochloric acid, then subjected to evaporation at reduced pressure. The residue was taken up in 200 ml of water and extracted with chloroform. Evaporation of this solvent left a syrupy residue, 55 g, which consisted of the compound diethyl (3-hydroxyquinucldin-2-yl)methyl-methylmalonate; its methiodide salt, prepared with methyl iodide in acetone, has a m.p. of 228.2°.

The foregoing product, 54.8 g was refluxed with concentrated hydrochloric acid, 200 ml. and water, 100 ml for 20 hours. Partial evaporation of the solvent and cooling induced the crystallization of 2-(trans-3-hydroxyquinuclidin-2-yl)-methylpropanoic acid hydrochloride, 8 g (18%), which is a by-product; m.p. 268.8°–269.4°. Further concentration of the mother liquor and cooling provoked the crystallization of the desired 4-methyl-6-oxa-1-azatricyclo (4.2.2.0$^{2,7}$) dodecan-5-one hydrochloride, 27.5 g, (66%), m.p. 267.2° with decomposition.

EXAMPLE 2

Ethyl phenylacetate, 49.2 g was added to a solution of sodium ethoxide previously prepared from metallic sodium, 2.9 g and ethanol, 100 ml. The mixture was cooled to 5°, then a solution of 2-methylenequinuclidin-3-one, 39.4 g, in ethanol, 50 ml. was added dropwise and with stirring. After 16 hours at room temperature, the solution was neutralized with acetic acid then subjected to evaporation at reduced pressure. Water, 100 ml. was added to the residue and the mixture was extracted with chloroform. Evaporation of this solvent gave ethyl (3-oxoquinuclidin-2-yl)methylphenylacetate, 54 g (60%); b.p. 195°–200° at 1 mm Hg; m.p. of methiodide salt, 194.7°–195.6°.

The foregoing compound, 22.4 g was dissolved in ethanol, 100 ml, and the resulting solution was treated at 5° with a solution of sodium borohydride 1.2 g in ethanol 200 ml. The borohydride solution was added in small increments over a period of 6 hr. After 20 hr, the mixture was neutralized with concentrated hydrochloric acid then subjected to evaporation at reduced pressure. The residue was taken up in 200 ml water and extracted with chloroform. Evaporation of this solvent gave Ethyl (3-hydroxyquinuclidin-2-yl) methyl-phenylacetate, 19.5 g, (80%), m.p. 147.7°–148.2° after recrystallization from acetone.

The foregoing compound, 16.9 g, was refluxed in a mixture of concentrated hydrochloric acid, 100 ml and water, 40 ml for 20 hr. Evaporation of the solvent under reduced pressure left a glassy residue which was redissolved in water, 50 ml neutralized with sodium bicarbonate and extracted with chloroform. Evaporation of this solvent left a residue which, when triturated with petrol ether, gave crystalline 4-phenyl-6-oxa-1-azatricyclo(6.2.2.0$^{2,7}$) dodecan-5-one, 2.7 g (18%), m.p. 162°–163°.

By procedures similar to those described under the foregoing examples, analogous compounds may be prepared. A number of compounds thus prepared are given in the following list:

| Compound | Melting Point Base Compound | Boiling Point HCl Salt |
| --- | --- | --- |
| 6-oxa-1-azatricyclo(6.2.2.0$^{2,7}$)dodecan-5-one | 86.7° | |
| 4-methyl-6-oxa-1-azatricyclo(6.2.2.0$^{2,7}$)dodecan-5-one | 102° | 267.2° |
| 4-ethyl-6-oxa-1-azatricyclo(6.2.2.0$^{2,7}$)dodecan-5-one | *65° | 255–256° |
| 4-isopropyl-6-oxa-1-azatricyclo(6.2.2.0$^{2,7}$)dodecan-5-one | 130° | 180.6–182.7° |
| 4-n-butyl-6-oxa-1-azatricyclo(6.2.2.0$^{2,7}$)dodecan-5-one | 77.4° | |
| 4-n-benzyl-6-oxa-1-azatricyclo(6.2.2.0$^{2,7}$)dodecan-5-one | 159.6–160.2° | 282° (dec.) |
| 4-p-methylphenyl-6-oxa-1-azatricyclo(6.2.2.0$^{2,7}$)dodecan-5-one | 143.1–143.9° | above 300° |
| 4-p-chlorophenyl-6-oxa-1-azatricyclo(6.2.2.0$^{2,7}$)dodecan-5-one | 186.8–187.6° | above 300° |
| 4-m-methoxyphenyl-6-oxa-1-azatricyclo(6.2.2.0$^{2,7}$)dodecan-5-one, free base | 144.8° | |

*methiodide salt melting at 158.1° C.

EXAMPLE 3

1-azatricyclo (6.2.2.0$^{2,7}$)-4-phenyl dodecan-5-one

The compound 1,4-ethano-6-oxo-7-phenyl-1,2,3,4,6,7,8,8a-octahydroquinoline was prepared by a modification of the method of Oppenheimer and Bergmann, Synthesis 269 (1972) as follows:

To a solution prepared from 3 g sodium metal in 100 ml absolute methanol there was added 45 g methyl benzyl ketone. The resulting solution was refluxed for 30 minutes, cooled to 0° C and 39 g 2-methylene-3-quinuclidinone was added. The solution was stirred at ambient temperature during 48 hours, neutralized by the addition of 3 ml acetic acid and the solvents were removed under reduced pressure. There was obtained a crude oil which was extracted with chloroform. After evaporation of the solvent there was obtained 52 g (a yield of 60%) of the desired product, M.P. from acetone, 125.7° C. Treatment with hydrochloric acid gave the corresponding hydrochloride salt, M.P. above 300° C (dec.).

The double bond in the above compound was subjected to selective reduction by dissolving 15 g of the free base in 150 ml ethanol and reducing with hydrogen at 3 atmospheres in the presence of 0.5 g of 10 percent palladium on carbon in a Parr apparatus. After 48 hours the solution was filtered off and evaporated. The residue was recrystallized from acetone, M.P. = 122.6° C. Treatment with gaseous hydrogen chloride in acetone gave the hydrochloride salt of 1-azatricyclo (6.2.2.0$^{2,7}$)-4-phenyl dodecan-5-one in almost quantitative yield, M.P. above 300° C (dec.).

EXAMPLE 4

1-azatricyclo (6.2.2.0$^{2,7}$)-4-ethyl dodecan-5-one

This compound hydrochloride was prepared by catalytic hydrogenation of the double bond in 1,4-ethano-6-oxo-7-ethyl-1,2,3,4,6,7,8,8a-octahydroquinoline by a modification of the method of Oppenheimer and Bergmann (see Ex. 3). To a solution of 1 g sodium metal in 100 ml ethanol there was added 6.3 g -ethylacetoacetate. The resulting solution was refluxed during 30 minutes, cooled to 0° C and 5.5 g 2-methylene-3-quinuclidinone was added. The solution was stirred overnight at room temperature, neutralized with acetic acid and the solvents were evaporated. The residue was extracted with toluene which was subsequently removed. The extract was treated with 17 ml concentrated hydrochloric acid and 5 ml of water under reflux during 7 hours. Evaporation of the solvent and trituration with ethanol induced crystallization of the hydrochloride salt of 1,4-ethano-6-oxo-7-ethyl-1,2,3,4,6,7,8,8a-octahydroquinoline, M.P. above 300° C (dec.). The free base, M.P.=63.5° C may be purified by distillation under reduced pressure, B.P., 3mm Hg: 148° C. Yield: 60 percent.

The double bond for the foregoing compound was selectively reduced as follows: 10 gms. of the free base were dissolved in 100 ml. ethanol; 0.5 gm. of 10% palladium on carbon were added and the suspension was shaken under hydrogen at 3 atmospheres in a Parr apparatus. After 48 hours, the suspension was filtered and the clear filtrate was evaporated to dryness. The residue consisted of 1-azatricyclo (6.2.2.0^{2,7})-4-ethyldodecan-5-one in almost quantitative yield. The melting point of the hydrochloride salt is 291°–292°.

The compounds of the present invention of Formula III, wherein X is $CH_2$, have pharmacological properties analogous to the compounds of Formula II, wherein X is =O. They are of special value as psychomotor stimulants; they are effective antagonists against the depressant effects of barbiturates and prevent tremors in animals pretreated with oxotremorine they are effective in a dosage range of 0.3 mg. to 3.0 mg. per kg. Since their metabolism proceeds along pathways different from that of the corresponding compounds having the valerolactone structure, they may be used in combination therapy, as adjuncts or synergists for each other in pharmaceutical preparations incorporating the two types of compounds.

ACUTE TOXICITY

The median lethal toxicity dosage of compounds of the present invention was determined by the procedure of Litchfield et al., J. Pharmacol. Exp. Ther. 96, 39 (1949). In each experiment at least five groups of six mice each were used for each dosage and the $LD_{50}$ was determined at 95 percent confidence limits.

Guinea Pig Ileum Test

Peripheric antimuscarinic activity was assayed by the cummulative dose response procedure of Kuhnen-Clausen, Toxicol. App. Pharmacol. 23, 443 (1972).

Oxotremorine Antagonism Test

This was carried out according to Brinclecombe et al., J. Pharm. Pharmaol. 23, 745–757 (1971).

An examination of compounds of the present invention has shown that the mean median lethal dose of the hydrochloride salts in mice after subcutaneous injection in saline solution, is within the range of 75 mg to 273 mg/kg body weight. The most toxic compounds are those where R=ethyl and the least toxic are those where R=phenyl.

The compounds are effective in preventing tremors induced in mice by the administration of 200 micrograms oxotremorin per mouse (intraperitoneally). The median dosage for Compounds II and III wherein R=ethyl is 3 mg/kg by subcutaneous injection; that of Compound II with R=phenyl is 6 mg/kg and for III with R=phenyl the dosage is 0.6 mg/kg. Thus, the therapeutic index for this particular effect is 25 to 50, and 86 for the last mentioned compound. The equipotent molar ratio with respect to atropine is 10 to 8, respectively. Compared with atropine, the peripheral anti-cholinergic effect of the compounds of the invention is negligible. For example, the equipotent molar ratio in the prevention of contraction of the guinea pig ileum is: Atropine: 1 ; Compound II with R=ethyl: 7200; Compound II with R=phenyl: 9000; Compound III with R=ethyl: 1300; R=phenyl:1700. Thus, the central effect of the compounds of the present invention is far more pronounced than their peripheral effects. The ratio of central to peripheral activity for atropine is 1:35, whereas the ratio for compounds of the present invention is 3:1 according to Inch et al., J. Phar. Phamacol. 25, 359 (1973).

Amongst other effects of compounds of the present invention there may be mentioned rapid mydriasis on topical application of solutions to the eye. For example, a 2 percent solution to the eye of a rabbit resulted in an onset of mydriasis after 8 to 10 minutes, and the effect lasted for about an hour. Injection into mice resulted in a slight hyperthermia (not exceeding +0.8° C), and this reached a maximum after 20 minutes. Increased psychomotor activity was found with mice, evident from the rate of rearing. A potentiation of the effect of nicotine was found upon application to the superior cervical ganglion of the cat. Fasciculation of striated muscle are induced only by very high doses, verging on the mean lethal dose.

What is claimed is:

1. A compound selected from the group consisting of compounds of the formula:

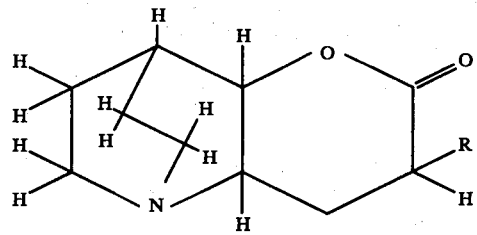

wherein R is selected from the group consisting of hydrogen, lower alkyl, cyclopentyl, cyclohexyl, thienyl, phenyl, methylphenyl, methoxyphenyl, chlorophenyl, trifuloromethylphenyl, aminophenyl, di-loweralkylamino phenyl and benzyl, and physiologically acceptable salts thereof.

2. 4-Methyl-6-oxa-1-azatricyclo (6.2.2.0^{2,7}) dodecan-5-one and its hydrochloride salt.

3. A compound of claim 1, 4-phenyl-6-oxa-1-azatricyclo(6.2.2.0^{2,7})dodecan-5-one and its salts.

4. A compound of claim 1, 6-oxa-1-azatricyclo (6.2.2.0^{2,7}) dodecan-5-one and its salts.

5. A compound of claim 1, 4-methyl-6-oxa-1-azatricyclo (6.2.2.0^{2,7}) dodecan-5-one and its salts.

6. A compound of claim 1, 4-ethyl-6-oxa-1-tricyclo (6.2.2.0^{2,7}) dodecan-5-one and its salts.

7. A compound of claim 1, 4-isopropyl-6-oxa-1-azatricyclo (6.2.2.0^{2,7}) dodecan-5-one and its salts.

8. A compound of claim 1, 4-n-butyl-6-oxa-1-azatricyclo (6.2.2.0^{2,7}) dodecan5-one and its salts.

9. A compound of claim 1, 4-benzyl-6-oxa-1-azatricyclo (6.2.2.0^{2,7}) dodecan-5-one and its salts.

10. A compound of claim 1, 4-p-methylphenyl-6-oxa-1-azatricyclo (6.2.2.0^{2,7}) dodecan-5-one and its salts.

11. A compound of claim 1, 4-p-chlorophenyl-6-oxa-1-azatricyclo (6.2.2.0^{2,7}) dodecan-5-one and salts thereof.

12. A compound of claim 1, 4-m-methoxyphenyl-6-oxa-1-azatricyclo (6.2.2.0^{2,7}) dodecan-5-one and its salts.

13. A pharmaceutical preparation for psychomotor stimulation comprising a therapeutically sufficient quantity of a compound of claim 1 and a pharmaceutically acceptable carrier therefor.

14. A pharmaceutical preparation for psychomotor stimulation comprising from 10 mg. to 100 mg. of a compound of claim 1 per unit dose and a pharmaceutically acceptable carrier therefor.

15. A pharmaceutical mydriatic solution comprising a therapeutically sufficient quantity of the compound of claim 1 dissolved in an essentially aqueous solvent.

* * * * *